United States Patent [19]

Sung et al.

[11] Patent Number: 4,518,782

[45] Date of Patent: May 21, 1985

[54] FUEL COMPOSITIONS CONTAINING N-ALKYL GLYCYL IMIDAZOLINE

[75] Inventors: Rodney L. Sung, Fishkill; Benjamin J. Kaufman, Wappingers Falls; Peter Dorn, LaGrangeville, all of N.Y.

[73] Assignee: Texaco Inc., White Plains, N.Y.

[21] Appl. No.: 291,583

[22] Filed: Aug. 10, 1981

[51] Int. Cl.³ .................... C07D 233/06; C10L 1/14
[52] U.S. Cl. ...................... 548/353; 44/63; 548/97; 548/238; 544/162; 544/400
[58] Field of Search ........................ 548/353

[56] References Cited

U.S. PATENT DOCUMENTS

Re. 23,227  5/1950  Rasp et al. ............... 548/353
4,000,079  12/1976  Blair, Jr. et al. .......... 548/353

Primary Examiner—Donald G. Daus
Assistant Examiner—S. A. Gibson
Attorney, Agent, or Firm—Robert A. Kulason; James F. Young; James J. O'Loughlin

[57] ABSTRACT

Disclosed are fuel compositions including alcohol-extended fuels containing friction-reducing, anti-corrosion and detergent amounts of at least one fuel soluble glycine derivative of the formula:

$$RNHCH_2X$$

wherein R is a hydrocarbyl group having 6 to 18 carbons and X is

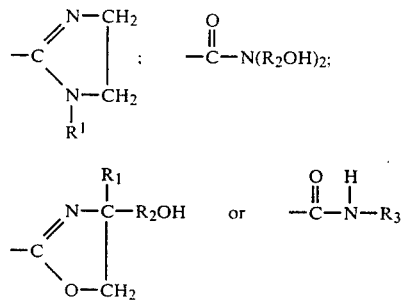

wherein $R_1$ is lower alkyl having 1 to 5 carbon atoms; $R_2$ is alkylene having 1 to 5 carbon atoms; $R_3$ is an alkylamino or alkylpolyamino group having 1 to 5 carbon atoms.

3 Claims, No Drawings

FUEL COMPOSITIONS CONTAINING N-ALKYL GLYCYL IMIDAZOLINE

BACKGROUND OF THE INVENTION

1. Field of the Invention

This invention relates to hydrocarbon fuels including alcohol-extended fuels and more particularly to fuels comprising a mixture of hydrocarbons in the gasoline boiling range and glycine derivatives which provide carburetor detergency and reduce friction between sliding metal surfaces in internal combustion engines.

To conserve crude oil, auto manufacturers have been urged by various governments to provide motor vehicles having increased gasoline mileage. To realize this goal, one approach used has been to design smaller, lighter and aerodynamically more efficient vehicles.

Another approach which can be combined with the first one is to develop energy-saving fuel additives and to use the modified fuel in internal combustion and similar engines.

Another consideration with fuels is that they have a tendency to form polymeric materials (variously called "gum" or "sludge" or "varnish") in various parts of fuel systems. These resin-like deposits tend to form in the fuel supply lines, fuel filter, carburetor, fuel control injectors, intake manifold and valve stems. Such deposits are objectionable not only because of their effect on mechanical performance but also because they decrease the breathing efficiency in engines of the spark ignition type.

Although each type of fuel is composed essentially of hydrocarbons their stability characteristics differ considerably. Thus typical automotive fuels contain straight and branched chains compounds while aircraft fuels contain a smaller proportion of olefins. Currently, certain types of fuels contain increased amounts of cracked stocks resulting in a higher olefin content and an increased susceptibility to the formation of gum.

It would be advantageous to use multipurpose additives which provide detergency, energy-saving, and anticorrosion properties to a fuel. Such additives are provided by the present invention.

2. Description of Prior Disclosures

Coassigned U.S. Pat. No. 4,266,944 discloses fuel compositions containing acyl glycine oxazolines. U.S. Pat. Nos. 4,035,309; 4,049,564 and 4,153,566 disclose oleaginous compositions containing oxazoline reaction products of dicarboxylic acids, esters or anhydrides with 2,2-disubstituted-2-amino-1-alkanols which are useful sludge dispersants and anti-rust agents.

Coassigned U.S. Pat. No. 3,773,479 describes a motor fuel composition comprising a mixture of hydrocarbons in the gasoline boiling range containing a minor amount of a substituted asparagine to provide carburetor detergency and anti-icing properties to the fuel.

SUMMARY OF THE INVENTION

The invention provides additives which can be represented by the following general formula:

RNHCH$_2$X wherein R is a hydrocarbyl group having 6 to 18 carbons such as CoCo(C$_{11}$H$_{23}$), oleo (C$_{17}$H$_{33}$) or tallow (C$_{16}$H$_{31}$ and C$_{18}$H$_{35}$) groups and X is:

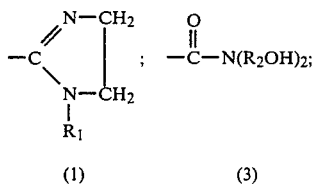

(1)        (3)

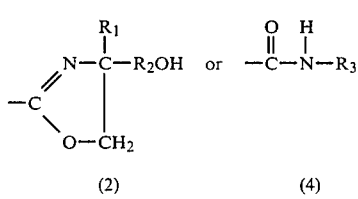

(2)        (4)

wherein R$_1$ is lower alkyl having 1 to 5 carbon atoms; R$_2$ is alkylene having 1 to 5 carbon atoms; R$_3$ is an alkylamino or having 1 to 5 carbon atoms or an alkyl polyamino group having 1 to 5 carbon atoms and up to 2 amino groups per carbon atom.

Preferably, the R$_1$, R$_2$ and R$_3$ radicals are straight chain, however, they also can be branched and may be substituted with one or more non-interfering substituents such as halogen, cyano, trifluoromethyl, nitro or alkoxy as long as these are inert under the preparative conditions used to synthesize the compounds.

The present invention also provides a motor fuel composition suitable for a spark-ignited internal combustion containing a minor, detergent and friction-reducing amount of at least one of the above compounds; preferably, this amount ranges from about 5 to about 200 parts per thousand barrels of fuel.

DETAILED DESCRIPTION OF THE INVENTION

The preparation of the additives of the invention can be readily and easily conducted using commercially available starting materials.

The additives where X is 1 or 2, above, preferably are synthesized by reacting approximately stoichiometric amounts of chloroacetic acid, at least one amine of the formula RNH$_2$ and pyridine serving as a scavenger to remove hydrochloric acid formed in the reaction in a mixed inert solvent preferably consisting of equal parts by volume of xylene and hexane. The reaction is refluxed, filtered and cooled and, then again refluxed with a primary amine or diamine. The reaction proceeds as follows:

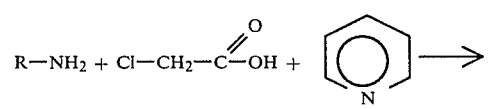

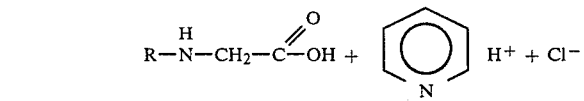

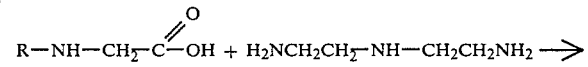

-continued

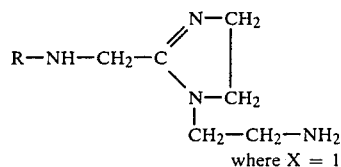
where X = 1

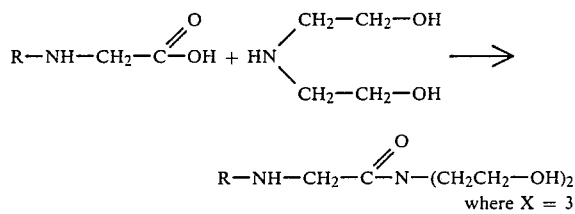

The additives where X is 3 or 4, above, are prepared preferably by refluxing approximately stoichiometric amounts of chloroacetic acid and of at least one amine of the formula RNH₂ in a mixed inert solvent preferably consisting of equal parts by volume of xylene and hexane in the presence of sodium carbonate serving to remove hydrochloric acid formed in the reaction. The water of reaction is azeotroped and the intermediate formed thereafter is refluxed with a hydroxyalkylamine or a polyamine.

The reaction proceeds as follows:

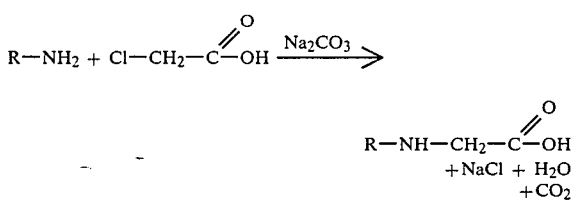

Then where x = 3:

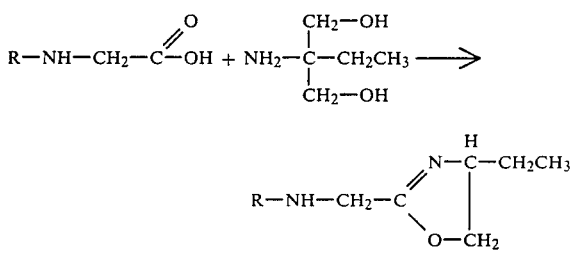

or where x = 4:

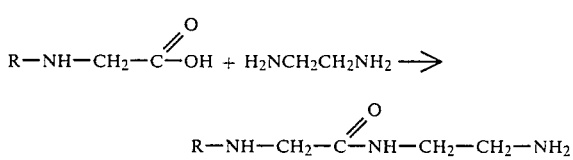

The preferred starting primary amines or "Armeens" are commercially available from the Armak Company and have a primary amino group attached to the terminal carbon of the straight chain saturated or unsaturated hydrocarbyl group.

Preferred amines include Armeen "C" (cocoamine) having a typical chain length distribution from $C_6$ to $C_{18}$ with 50% saturated $C_{12}$ alkyl; Armeen "O" (oleylamine) having a typical chain length distribution of $C_{14}$ to $C_{18}$ with 76% being oleyl; and Armeen T, (tallowamine) with a chain length distribution ranging from $C_{12}$ to $C_{18}$ with 29% of $C_{16}$ saturated groups.

The invention is further illustrated by the following examples in which all proportion are by weight unless otherwise specified.

EXAMPLE I

Synthesis of N-Tallow Glycyl Imidazoline of diethylene-triamine

To 275 parts of Armeen T (Tallow amine) 79 parts of pyridine in a mixture of solvents (400 parts xylene and 400 parts hexane), 95 parts of chloroacetic acid were added. The mixture was refluxed for 3 hours. Then it was filtered and cooled. The resulting mixture was divided into 2 halves. To one half (1A) was added 77 parts of diethylene-triamine. (The other half (1B) was used to identify the intermediate). The resulting mixture was refluxed and the water of reaction was azeotroped. The reaction was stopped after no more water azeotroped. The reaction mixture was filtered and stripped under vacuum. Elemental analysis and IR data of the product confirmed the structure:

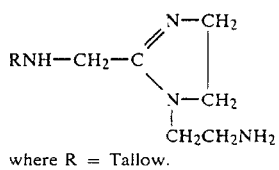
where R = Tallow.

EXAMPLE II

Synthesis of N-Tallow Glycyl Oxazoline of 2-amino-2-ethyl-1,3-propanediol

To a 200 parts hexane and 200 parts xylene solution containing 137.5 parts of Armeen T, 39.5 parts pyridine, 47.5 parts of chloroacetic acid were added slowly in small portions. After the addition of chloroacetic acid was completed, the reaction mixture was refluxed for 3 hours. To the cooled reaction mixture were added 59.5 parts of 2 amino-2-ethyl-1,3-propanediol. The mixture was then refluxed until no more water was azeotropically removed. The mixture was filtered and stripped under vacuum to give a product whose elemental analysis and I.R. data confirmed the structure:

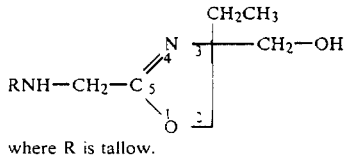
where R is tallow.

EXAMPLE III

N-Tallow glycyl amide of diethanolamine

To a mixture of 400 parts hexane and 400 parts xylene containing 276 parts of Armeen-T, 53 parts sodium carbonate, 94 parts of chloroacetic acid were added slowly. The reaction mixture then was heated to reflux and the water of reaction was azeotroped. After no more water came over the mixture was cooled and 104 parts of diethanolamine were added. The mixture was refluxed and azeotroped until no more water came over. It was next filtered and stripped. The product was analyzed by elemental analysis and I.R. which confirmed the structure:

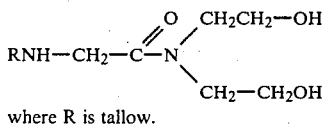

where R is tallow.

EXAMPLE IV

Synthesis of N-Tallow-glycyl amide of ethylene diamine

To 400 parts of xylene and 400 parts of hexane containing 275 parts of Armeen-T, 53 parts sodium carbonate, add slowly 95 parts chloroacetic acid in small portions. Reflux and azeotrope until no more water comes over. Then cool and add 60 parts of ethylene-diamine. Reflux and azeotrope until 18 parts of water comes over. Filter and strip. The product was analyzed by elemental analysis and I.R., confirming the structure:

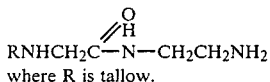

where R is tallow.

The following compounds which are effective in the present invention are prepared as in the preceeding examples:

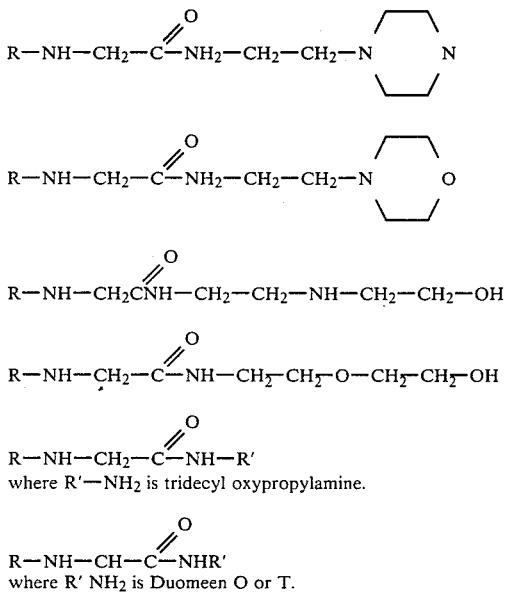

where R'—NH$_2$ is tridecyl oxypropylamine.

$$R-NH-CH-\overset{O}{\overset{\|}{C}}-NHR'$$

where R' NH$_2$ is Duomeen O or T.

Mixtures of the subject compounds also are effective in the present invention.

In general, the base fuel with which the additives are used, will consist of a mixture of hydrocarbons in the gasoline boiling range, i.e., boiling from about 75° to 450° C. The hydrocarbon components can consist of paraffinic, naphthenic, aromatic and olefinic hydrocarbons. This gasoline can be obtained naturally or it can be produced by thermal or catalytic cracking and/or reforming of petroleum hydrocarbons. The base fuel will generally have a Research Octane Number about 85 and up to about 102 with the preferred range being from about 90 to 100.

The base fuel can also be of the type extended with up to 20% by volume of a lower alkanol (C$_1$–C$_4$) such as methanol or ethanol.

The additives of the invention were evaluated by various tests.

One such test is the Chevrolet Carburetor Detergency Test Phase III.

This test is run on a Chevrolet V-8 engine mounted on a test stand using a modified four-barrel carburetor. The two secondary barrels of the carburetor are sealed and the feed to each of the primary barrels arranged so that separate fuels can be run in each barrel simultaneously. The primary carburetor barrels are also modified so that they have removable aluminum inserts in the throttle plate area in order that deposits formed on the inserts in this area can be conveniently weighed.

In this procedure designed to determine the effectiveness of an additive fuel to remove preformed deposits in the carburetor, the engine is run for a period of time, usually 24 to 48 hours, using the base fuel as the feed to both barrels with engine blow-by circulated to the air inlet of the carburetor. The weight of the deposits on both sleeves is determined and recorded. The engine is then recycled for 24 additional hours with a reference fuel being fed to one barrel, additive fuel to the other, and no blow-by to the carburetor air inlet. The reference fuel contains 15 PTB of a carburetor detergent. The inserts are then removed from the carburetor and weighed to determine the difference between the performance of the additive and non-additive fuels in removing the preformed deposits. After the aluminum inserts are cleaned, they are replaced in the carburetor and the process repeated with the fuels reversed in the carburetor to minimize differences in fuel distribution and barrel construction. The effectiveness of the additive fuel is expressed as the difference Δ between deposit removed by the additive fuel and the deposit removed by the base fuel. When Δ is positive, the additive fuel has removed more deposit than the reference fuel.

The motor fuel used as a standard for comparison purposes in the test is a commercial high octane premium gasoline containing a highly effective carburetor detergent. The fuel composition representative of the invention consisted of Base Fuel A described above containing the indicated amounts of the additive of the invention. The results of this test are reported as the difference in carburetor deposits removed by the additive containing gasoline of the invention in comparison to the commercial premium detergent gasoline.

The results of the Chevrolet Carburetor Detergency Tests are set forth in the following Table I.

TABLE I

| Run No. | Additive in S.C. + 3 g./gal lead | Additive Fuel | Reference Fuel (1) | Δ |
|---|---|---|---|---|
| 1 | 0.20(v) % commercial product containing 15 PTB[a] of detergent A | 41 | +10[b] | +51 vs. A |
| 2 | 100 PTB N—Armeen-T glycyl oxazoline of 2-amino-2 ethyl-1,3-propanediol (Ex. 11) | 74 | 84 | −10 vs. B |
| 3 | 100 PTB N—Armeen-T glycyl imidazoline of diethylene triamine (Ex. 1A) | 88 | 89 | −1 vs. B |

TABLE I-continued

| Run No. | Additive in S.C. + 3 g./gal lead | Additive Fuel | Reference Fuel (1) | Δ |
|---|---|---|---|---|
| 4 | 20 PTB N—Armeen T glycyl imidazoline of diethylene triamine (Ex. 1B) | 79 | 65 | +14 vs. D |
| 5 | 20 PTB N—Armeen T glycyl oxazoline of 2-amino-2 ethyl-1,3-propane diol (Ex. 11) | 55 | 66 | −11 vs. D |
| 6 | 0.218 (v) % Commercial product containing 50 PTB of Lubrizol J80 detergent | 45 | 88 | −43 vs. B |
| 7 | 0.2 (V) % commercial product containing 15 PTB of detergent A | 41 | 40 | −1 vs. C |
| 8 | 0.2 (V) % commercial detergent A | 48 | 47 | −1 vs. E |
| 9 | 20 PTB Example IV material | 80 | 53 | +27 vs. E |
| 10 | 20 PTB N—Armeen T Glycyl amide of diethanol amine (Ex 111) | 75 | 52 | +23 vs. E |

(1) Reference Fuels: A = Fuel, B = 1035 PTB Chevron Co. F-310, C = 0.218 (V) % Commercial detergent A, D = 20 PTB experimental additive B, E = 10 PTB experimental additive B.
(a)Parts per thousand barrels
(b)+ denotes deposit build-up.
Detergent A is an additive package containing: N—butyl alcohol 15%, aromatic distillates 34%, polyisobutylenes 4%, polyisobutylenamines 9%. Additive B is the reaction product of maleic anhydride and Armeen L15 in solvent neutral oil oxidate and a carrier oil.

The data of Table I show the present additives to be better than or equivalent to the commercial additives.

The data indicate that 0.2(v)% of commercial detergent A removes 41% deposits, Chevron F-310 at 1035 PTB removes 89% deposit, N-Tallow-glycyl imidazole at 100 PTB removes 88% deposits and N-Tallow glycyl oxazole at 100 PTB removes 74% deposits compared with F-310 at 1035 PTB which removes 84% deposits. At 20 PTB the N-Tallow glycyl imidazoline (Δ = +14) and N-Tallow glycyl Oxazoline (Δ = −11) are better or comparable to experimental detergent B. N-Armeen-T glycyl amide of diethanolamine and ethylene diamine at 20 PTBs are better than B. In conclusion, N-alkyl glycyl amides are equivalent to Chevron F-310 equivalent or better than detergent B.

The additives of the invention are also effective in alcohol-extended fuels as shown by the Chevrolet Carburetor Detergency Test Phase III data given below in Table II. In this test the reference was a fuel containing 80 PTB of a detergent consisting of an oil diluted 2:1 mixture of N-oleyl 1,3-diaminopropane and N,N'-di(-N''-oleyl-aminopropyl)asparagine. The additive used was the N-oleyl glycylamide of ethylenediamine prepared as in Example IV.

TABLE II

| Additive | Fuel Composition | Δ vs. fuel + prior art additive |
|---|---|---|
| 20 PTB | add in 10 vol. % of C1-C4 alcohols and gasoline | Δ = +1.5 |
| 20 PTB | add in 5 vol. % methanol and gasoline | Δ = +3.5 |
| 20 PTB | add in gasohol | Δ = +2 |

The data of Table II show the additive of the invention to be superior to a fourfold amount of the prior art detergent.

The additives of the invention also have anti-corrosion properties as shown by their performance in the National Association of Corrosion Engineers (NACE) Rusting Test. In this test a determination is made of the ability of the gasoline to inhibit the rusting of ferrous parts when water becomes mixed with gasoline. Briefly stated, the test is carried out by stirring a mixture 300 ml of the test gasoline and 30 ml of water at 37.8° C. with a polished steel specimen completely immersed therein for a test period of 3½ hours. The percentage of the specimen that has rusted is determined by comparison with photographic standards. Further details of the procedure appear in NACE Standard TM-01-72 and ASTM D6651 1P-135 (Procedure A).

Table III below shows the results of this test for N-oleyl glycyl amide of ethylene-diamine at different concentrations in pounds per 1000 barrels (PTB) in and against an unleaded base fuel.

The data of Table III show that as little as 5 PTB of the additive substantially eliminates rusting.

TABLE III

| NACE RUST RATING | |
|---|---|
| Concentration | Rust Rating |
| 20 PTB | Trace to 1% |
| 10 PTB | Trace to 1% |
| 5 PTB | Trace to 1% |
| 2.5 PTB | Trace to 5% |
| Unleaded base fuel alone | 50 to 100% |

Two separate tests were carried out which demonstrate the ability of the present fuel composition to significantly improve fuel economy. These tests use a 1978 Buick Century equipped with a V-6 engine. The manual driving cycle is shown below:

MANUAL DRIVING CYCLE 60 minutes at 55 mph
60 minutes at 45 mph
45 minutes at 30 mph
15 minutes at idle
45 minutes at 15 mph
15 minutes at idle In addition, a level road load was used in back to back mileage testing. The results of the test using the oleyl-glycylamide of ethylene-diamine are shown in the second table and give the city, highway and EPA combined mileage per gallon. It should be noted that combined mileage is calculated according to the equation:

$$\frac{1}{\frac{.55}{\text{City mileage}} + \frac{.45}{\text{Hwy mileage}}}$$

| | BASE FUEL | | | |
|---|---|---|---|---|
| Test | City MPG | Hwy. MPG | Combined MPG | Avg. Combined MPG |
| 1 | 18.03 | 22.85 | 19.92 | |
| | | | | 9.99 |
| 2 | 18.17 | 23.00 | 20.07 | |

| | | -continued | | |
|---|---|---|---|---|
| | | $\dfrac{1}{\dfrac{.55}{\text{City mileage}} + \dfrac{.45}{\text{Hwy mileage}}}$ | | |
| | | ADDITIVE FUEL | | |
| Test | City MPG | Hwy. MPG | Combined MPG | Avg. Combined MPG | % imp. With Additive |
| 1 | 18.54 | 23.70 | 20.55 | | |
| | | | | 20.44 | 2.25 |
| 2 | 18.32 | 23.44 | 20.32 | | |

The gasoline in both the base fuel and additive fuel is lead-free gasoline with the only difference being the inclusion of 100 PTB of the above additive.

Significantly, it has been estimated that each one percent reduction in the consumption of gasoline in the U.S. alone would result in a saving of 20,000,000 or more barrels of crude annually.

The fuels of the invention may contain any other additive conventionally employed in gasoline. Tetraalkyl lead, antiknock additives, dyes, antioxidants and the like can be beneficially employed without materially affecting the additives of the invention.

What is claimed is:

1. A friction-reducing, corrosion-inhibiting and detergent compound of the formula:

RNHCH$_2$X wherein R is a hydrocarbyl group having 12 to 16 carbon atoms in the chain and X is

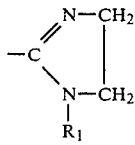

wherein R$_1$ is selected from the group consisting of hydrogen, a lower alkyl group having 1 to 5 carbon atoms and the radical —CH$_2$CH$_2$NH$_2$.

2. The compound of claim 1 wherein R is a oleo or tallow group.

3. The compound of claim 1 being the N-tallow glycyl imidazoline of diethylene triamine.

* * * * *